(12) United States Patent
Kooijman et al.

(10) Patent No.: US 9,812,287 B2
(45) Date of Patent: Nov. 7, 2017

(54) CHARGED PARTICLE MICROSCOPE WITH IMPROVED SPECTROSCOPIC FUNCTIONALITY

(71) Applicant: FEI Company, Hillsboro, OR (US)

(72) Inventors: Cornelis Sander Kooijman, Veldhoven (NL); Thijs Thomas Withaar, Eindhoven (NL); Gerard Nicolaas Anne van Veen, Waalre (NL)

(73) Assignee: FEI Company, Hillsboro, OR (US)

( * ) Notice: Subject to any disclaimer, the term of this patent is extended or adjusted under 35 U.S.C. 154(b) by 0 days.

(21) Appl. No.: 14/983,038

(22) Filed: Dec. 29, 2015

(65) Prior Publication Data

US 2016/0189922 A1    Jun. 30, 2016

(30) Foreign Application Priority Data

Dec. 30, 2014    (EP) .................................. 14200596

(51) Int. Cl.
*H01J 37/244*    (2006.01)
*H01J 37/285*    (2006.01)
(Continued)

(52) U.S. Cl.
CPC .......... *H01J 37/244* (2013.01); *G01N 23/223* (2013.01); *G01N 23/2252* (2013.01);
(Continued)

(58) Field of Classification Search
None
See application file for complete search history.

(56) References Cited

U.S. PATENT DOCUMENTS

| | | | |
|---|---|---|---|
| 6,462,332 B1 | 10/2002 | Trompenaars et al. | |
| 2010/0148064 A1* | 6/2010 | Harrach ................ | H01J 37/244 250/307 |

(Continued)

OTHER PUBLICATIONS

"Energy-Dispersive X-Ray Spectroscopy", Wikipedia, Accessed Dec. 29, 2015, 4 pages. <https://en.wikipedia.org/wiki/Energy-dispersive_X-ray_spectroscopy>.

(Continued)

*Primary Examiner* — Michael Logie
(74) *Attorney, Agent, or Firm* — Scheinberg & Associates, P.C.; Michael O. Scheinberg

(57) ABSTRACT

An improved spectroscopic analysis apparatus and method are disclosed, comprising directing a beam of radiation onto a measurement location on a specimen, thereby causing a flux of X-rays to emanate from this location; examining the X-ray flux using a detector arrangement, thus acquiring a spectrum; choosing a set of different measurement directions originating from the location; recording outputs from the detector arrangement for different measurement directions; adopting a spectral model that is a convoluted mix of terms B and $L_p$, where B is the Bremsstrahlung background spectrum and $L_p$ comprises spectral lines corresponding to the specimen composition at the measurement location; and then automatically deconvolving the set of measurements on the basis of the spectral model to calculate $L_p$ to determine the chemical composition of the specimen at the measurement location. The method includes corrections for differential X-ray absorption within the specimen along the different measurement directions.

19 Claims, 3 Drawing Sheets

Figure 1:
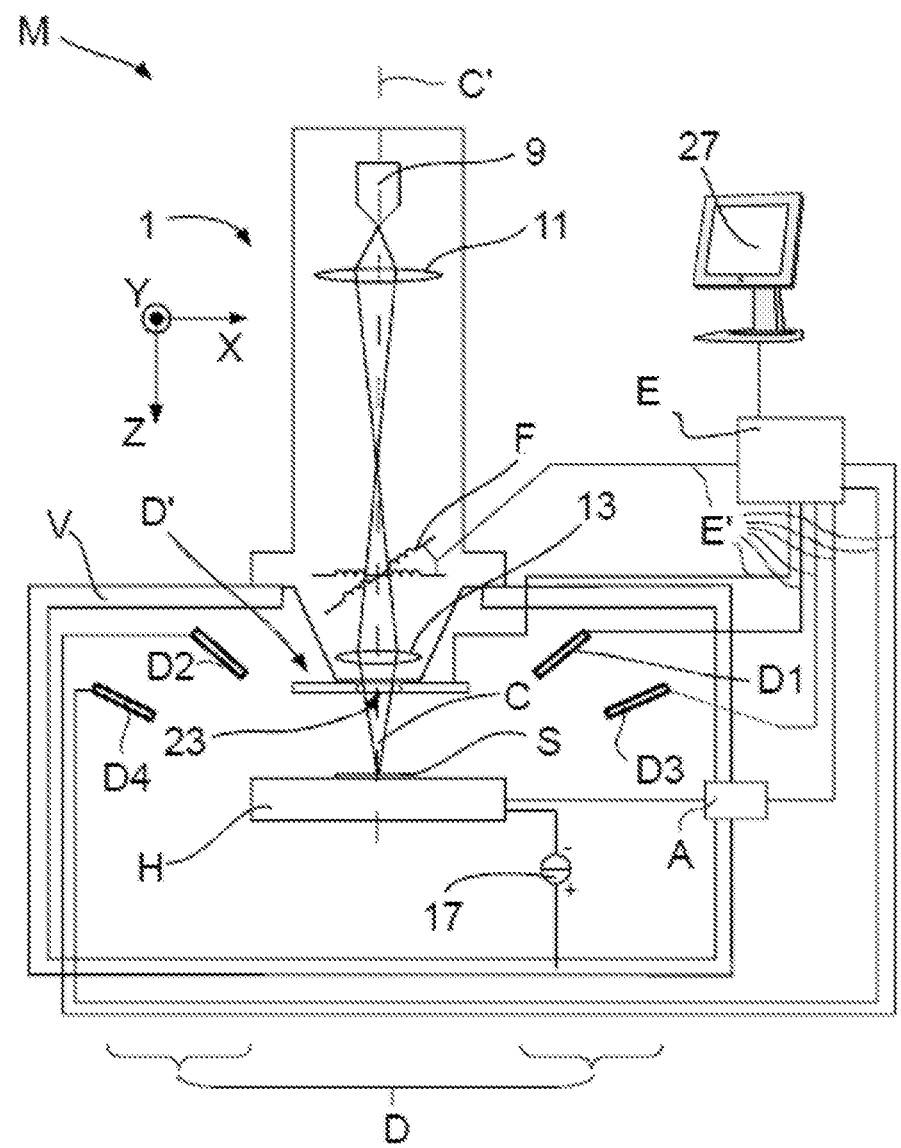

(51) Int. Cl.
*G01N 23/223* (2006.01)
*G01N 23/225* (2006.01)

(52) U.S. Cl.
CPC ........ *G01N 23/2257* (2013.01); H01J 37/285 (2013.01); *G01N 2223/501* (2013.01); *H01J 2237/2445* (2013.01)

(56) References Cited

U.S. PATENT DOCUMENTS

| | | | |
|---|---|---|---|
| 2011/0200164 A1* | 8/2011 | Blaj | G01N 23/046 378/4 |
| 2012/0288058 A1* | 11/2012 | Maeyama | G01N 23/207 378/46 |
| 2012/0326030 A1* | 12/2012 | Benner | H01J 37/244 250/310 |
| 2012/0326032 A1* | 12/2012 | Benner | H01J 37/244 250/310 |
| 2013/0277555 A1 | 10/2013 | Kooijman et al. | |
| 2015/0122992 A1 | 5/2015 | Owen et al. | |
| 2015/0155131 A1 | 6/2015 | Sluijterman et al. | |
| 2015/0262400 A1 | 9/2015 | Howell et al. | |

OTHER PUBLICATIONS

"Particle-Induced X-Ray Emission", Wikipedia, Accessed Dec. 29, 2015, 4 pages. <https://en.wikipedia.org/wiki/Particle-induced_X-ray_emission>.

"X-Ray Fluorescence", Wikipedia, Accessed Dec. 29, 2015, 12 pages. <https://en.wikipedia.org/wiki/X-ray_fluorescence>.

"X-Ray", Wikipedia, Accessed Dec. 29, 2015, 19 pages. <https://en.wikipedia.org/wiki/X-ray>.

"Electron Microscope", Wikipedia, Accessed Oct. 15, 2015, 11 pages. <https://en.wikipedia.org/wiki/Electron_microscope>.

"Scanning Electron Microscope", Wikipedia, Accessed Oct. 15, 2015, 18 pages. <https://en.wikipedia.org/wiki/Scanning_electron_microscope>.

"Transmission Electron Microscopy", Wikipedia, Accessed Oct. 15, 2015, 23 pages. <https://en.wikipedia.org/wiki/Transmission_electron_microscopy>.

"Scanning Transmission Electron Microscopy", Wkipedia, Accessed Oct. 15, 2015, 5 pages. <https://en.wikipedia.org/wiki/Scarining_transmission_electron_microscopy>.

"Scanning Helium Ion Microscope", Wkipedia, Accessed Oct. 15, 2015, 2 pages. <https://en.wikipedia.org/wiki/Scanning_Helium_Ion_Microscope>.

W. H. Escovitz et al., "Scanning Transmission Ion Microscope with a Field Ion Source", Proc. Nat. Acad. Sci. USA, vol. 72, No. 5, pp. 1826-1828, May 1975, 3 pages.

Frank Watt et al., "Microscopy with Protons", Innovation Magazine, Accessed Dec. 29, 2015, 3 pages. <http://www.innovationmagazine.com/volumes/v7n1/coverstory3.html>.

"Silicon Drift Detector", Wikipedia, Accessed Dec. 29, 2015, 1 page. <https://en.wikipedia.org/wiki/Silicon_drift_detector>.

"Mass Attenuation Coefficient", Wikipedia, Accessed Dec. 29, 2015, 4 pages. <https://en.wikipedia.org/wiki/Mass_attenuation_coefficient>.

L. A. Shepp et al., "Maximum Likelihood Reconstruction for Emission Tomography", IEEE Transactions on Medical Imaging, Oct. 1982, 10 pages.

William Hadley Richardson, "Bayesian-Based Iterative Method of Image Restoration", Journal of the Optical Society of America, Jan. 1972, 5 pages.

William H. Press et al., "Numerical Recipes in C: The Art of Scientific Computing", Chapter 10, Second Edition, 1992, 71 pages.

Peter J. Statham, "Limitations to Accuracy in Extracting Characteristic Line Intensities From X-Ray Spectra", Journal of Research of the National Institute of Standards and Technology, Nov. 1, 2002, 16 pages.

* cited by examiner

CHARGED PARTICLE MICROSCOPE WITH IMPROVED SPECTROSCOPIC FUNCTIONALITY

The invention relates to a method of examining a specimen using a spectroscopic apparatus, comprising the following steps:
  Providing the specimen on a specimen holder;
  Directing a focused input beam of radiation onto a location P on the specimen, thereby producing an interaction that causes a flux of X-rays to emanate from said location;
  Examining said flux using a detector arrangement, thus accruing a measured spectrum for said location.

The invention correspondingly relates to a spectroscopic apparatus comprising:
  A specimen holder, for holding a specimen;
  A source, for producing an input beam of radiation;
  An illuminator, for directing said beam so as to irradiate the specimen;
  A detector arrangement, for detecting a flux of X-rays emanating from the specimen in response to said irradiation;
  A computer processor, for performing at least one automated procedure in the apparatus.

The invention particularly relates to a situation in which said method is conducted in a charged particle microscope.

A method of the type described in the opening paragraph is known, for example, from the field of Energy-Dispersive X-ray Spectroscopy, which is often referred to using the acronyms EDX or EDS. In this technique, a specimen (often, but not necessarily, mineralogical in nature) is bombarded with a focused input beam of charged particles, e.g. in a Scanning Electron Microscope. A lower-shell electron in an atom of the specimen can be ejected from its orbit by a collision with one of these bombarding particles, creating an electron hole that is promptly filled by the de-excitation of a higher-shell electron in the atom in question, with the concurrent release of a quantum of energy in the form of an X-ray photon. The energy signature/distribution of photons emitted in this way will be characteristic of the particular electron shell structure of the atom in question, and can thus be used as a "fingerprint" in performing compositional analysis of the specimen. An energy-dispersive spectrometric detector collects, sorts and counts the different photons of different energies, producing a measured spectrum for the location of the specimen onto which the focused input beam was directed; such a spectrum can be rendered as a graph of counts per channel (ordinate) versus channel number (abscissa), corresponding to intensity versus energy, and generally comprising various peaks—whose energy can be used to identify the generating material (which may be an element, chemical compound or mineral, for example, and which may be amorphous or crystalline in nature, for example) and whose height can (in principle) be used to estimate relative quantity of the generating material. If desired, one can then (automatically) move the specimen and/or the beam so that the beam is directed onto a new location on the specimen, and (automatically) repeat the process described above at said new location. This technique is particularly useful in the field of mineralogy, in which a small specimen may contain many different kinds of minerals; however, its usefulness in fields such as metallurgy, microbiology and semiconductor science is also self-evident. For more information on EDX, reference is made to the following Wikipedia link, for example:
  en.wikipedia.org/wiki/Energy_Dispersive_Spectroscopy As here employed, the term EDX encompasses so-called Wavelength Dispersive X-Ray Spectroscopy (WDX or WDS). This latter technique can be regarded as a particular refinement of EDX in which the X-rays emerging from a specimen are filtered (e.g. with the aid of a particular type of crystal), so that only X-rays of a given wavelength are counted at any given time.

Another such technique is Proton-Induced X-Ray Emission (PIXE), in which the input beam comprises protons. This technique is described in more detail in the following reference, for example:
  en.wikipedia.org/wiki/PIXE In principle, PIXE can be performed in a proton microscope, or in a dedicated PIXE tool.

Yet another such known technique is X-Ray Fluorescence Spectroscopy, which is often referred to using the acronym XRF. This technique is similar to EDX, except in that the input beam comprises X-ray or gamma ray photons instead of charged particles. For more information on XRF, reference is made to the following webpage, for example:
  en.wikipedia.org/wiki/X-ray_fluorescence Some general information relating to X-rays can, for example, be gleaned from the following reference:
  en.wikipedia.org/wiki/X-ray As already alluded to above, (at least certain of) the aforementioned spectroscopic techniques can be conveniently performed in a charged particle microscope (CPM). Charged particle microscopy is a well-known and increasingly important technique for imaging microscopic objects, particularly in the form of electron microscopy. Historically, the basic genus of electron microscope has undergone evolution into a number of well-known apparatus species, such as the Transmission Electron Microscope (TEM), Scanning Electron Microscope (SEM), and Scanning Transmission Electron Microscope (STEM), and also into various sub-species, such as so-called "dual-beam" tools (e.g. a FIB-SEM), which additionally employ a "machining" Focused Ion Beam (FIB), allowing supportive activities such as ion-beam milling or Ion-Beam-Induced Deposition (IBID), for example. More specifically:
  In a SEM, irradiation of a specimen by a scanning electron beam precipitates/stimulates emanation of "auxiliary" radiation from the specimen, in the form of secondary electrons, backscattered electrons, X-rays and photoluminescence (infrared, visible and/or ultraviolet photons), for example; one or more components of this emanating radiation is/are then detected and used for image accumulation purposes, spectroscopy (such as EDX), etc.
  In a TEM, the electron beam used to irradiate the specimen is chosen to be of a high-enough energy to penetrate the specimen (which, to this end, will generally be thinner than in the case of a SEM specimen); the flux of transmitted electrons emanating from the specimen can then be used to create an image, spectrum, etc. When such a TEM is operated in scanning mode (thus becoming a STEM), an image can be accumulated during a scanning motion of the irradiating electron beam.

More information on some of the topics elucidated here can, for example, be gleaned from the following Wikipedia links:
  en.wikipedia.org/wiki/Electron_microscope
  en.wikipedia.org/wiki/Scanning_electron_microscope en.wikipedia.org/wiki/Transmission_electron_microscopy en.wikipedia.org/wiki/Scanning_transmission_electron_microscopy As an alternative to the use of electrons as irradiating beam, charged particle microscopy can also be performed using other species of charged particle. In this respect, the phrase "charged particle" should be broadly interpreted as encompassing electrons, positive ions (e.g. Ga or He ions), negative ions, protons and positrons, for instance. As regards ion-based microscopy, some further information can, for example, be gleaned from sources such as the following:

en.wikipedia.org/wiki/Scanning_Helium_Ion_Microscope

W. H. Escovitz, T. R. Fox and R. Levi-Setti, *Scanning Transmission Ion Microscope with a Field Ion Source*, Proc. Nat. Acad. Sci. USA 72(5), pp. 1826-1828 (1975).

www.innovationmagazine.com/innovation/volumes/v7n1/coverstory3.shtml

In all cases, a CPM (and, more generally, a spectroscopic apparatus as referred to above) will comprise at least the following components:

A radiation source, such as a Schottky electron source or ion gun.

An illuminator, which serves to manipulate a "raw" radiation beam from the source and perform upon it certain operations such as focusing, aberration mitigation, cropping (with an aperture), filtering, etc. It will generally comprise one or more (charged-particle) lenses, and may comprise other types of (particle-) optical component also. If desired, the illuminator can be provided with a deflector system that can be invoked to cause its output beam to perform a scanning motion across the specimen being investigated.

A specimen holder, on which a specimen under investigation can be held and positioned (e.g. tilted, rotated). If desired, this holder can be moved so as to effect scanning motion of the beam w.r.t. the specimen. In general, such a specimen holder will be connected to a positioning system such as a mechanical stage.

A detector arrangement (for detecting radiation emanating from an irradiated specimen), which can take many different forms, depending on the radiation being detected. Examples include (one or more of) photomultipliers (including solid state photomultipliers, SSPMs), photodiodes, CMOS detectors, CCD detectors, photovoltaic cells, etc., which may, for example, be used in conjunction with a scintillator film, for instance. In the specific case of X-ray detection, use is typically made of a so-called Silicon Drift Detector (SDD), or a Silicon Lithium (Si(Li)) detector, for example: see, for more information:

en.wikipedia.org/wiki/Silicon_drift_detector en.wikipedia.org/wiki/X-ray_fluorescence#Si.28Li.29_detectors Such a CPM/spectroscopic apparatus will also generally comprise:

A computer processor (and associated circuitry), for regulating operation of the apparatus, executing control commands, performing data processing, etc.

In the case of a transmission-type CPM (such as a (S)TEM, for example), the apparatus/tool will also comprise:

An imaging system, which essentially takes charged particles that are transmitted through a specimen (plane) and directs (focuses) them onto analysis apparatus, such as a detection/imaging device, spectroscopic apparatus (such as an EELS module), etc. As with the illuminator referred to above, the imaging system may also perform other functions, such as aberration mitigation, cropping, filtering, etc., and it will generally comprise one or more charged-particle lenses and/or other types of particle-optical components.

In what follows, the invention may—by way of example—sometimes be set forth in the specific context of electron microscopy. However, such simplification is intended solely for clarity/illustrative purposes, and should not be interpreted as limiting.

A problem with spectroscopic methods/apparatus as referred to above is that the spectra they produce are intrinsically "corrupted", making it difficult to use them as a basis for quantitative analysis. In the case of XPS and PIXE, for example, such corruption arises from the fact that particles in the input beam not only produce "Bohr-type" energy transitions between the energy levels of atoms in the specimen, but also inevitably produce "non-Bohr-type" events, whereby an input particle undergoes kinematic energy loss (e.g. due to retardation/deceleration) accompanied by a release of photonic energy (to balance energy and momentum rules). Whereas such Bohr-type transitions produce a valuable discrete spectrum (characteristic line spectrum) that is indicative of the chemical constitution of the specimen, the attendant non-Bohr-type events produce a continuous spectrum of a spurious nature, which basically represents unwanted "pollution" of said discrete spectrum—making it difficult, for example, to accurately determine peak heights therein. Such non-Bohr-type radiation is often referred to as "Bremsstrahlung". In the case of XRF, a certain amount of Bremsstrahlung is also typically present, though this is characteristically produced in the source of the input beam rather than in the specimen.

It is an object of the invention to address this issue. More specifically, it is an object of the invention to provide a spectroscopic method/apparatus that more accurately lends itself to quantitative spectral analysis. In particular, it is an object of the invention that such a method/apparatus should allow "extraction" of Bremsstrahlung contributions from spectral data, so as to allow characteristic line spectra to be more easily examined.

These and other objects are achieved in a method as set forth in the opening paragraph above, characterized by the following steps:

Choosing a set of mutually different measurement directions $d=\{d_n\}$ that originate from P, where n is a member of an integer sequence;

Recording an output $O_n$ of said detector arrangement for different values of $d_n$, thus compiling a measurement set $M=\{(O_n, d_n)\}$;

Adopting a spectral model $O_n'$ for $O_n$ that is a convoluted mix of (at least) terms B and $L_p$, where:

B is a substantially continuous spectral component associated with Bremsstrahlung;

$L_p$ is a substantially discrete spectral component associated with the composition of the specimen at location P;

Using computer processing apparatus to automatically deconvolve the measurement set M on the basis of said spectral model $O_n'$ and distill $L_p$ therefrom.

The basic gist of the invention is to treat the spectrum acquisition process as a (non-linear) multi-variable convoluted problem, in which (at least) certain variables demonstrate a (fundamentally different) functional dependence on emission direction of X-ray flux from P. By collecting spectral measurements for a variety of such emission directions (which thereby become the measurement directions d={$d_n$} referred to above), one acquires a data set that can be used as a basis for a deconvolution technique; more particularly, one can "disentangle" the convoluted data by solving an array of simultaneous optimization tasks, consistent with a chosen mathematical model $O_n'$. To give an analogy: in Analysis, an equation in several variables can be solved if it is a member of a set of simultaneous equations with a cardinality equal to the number of variables involved; in the current situation, deliberately acquiring spectral data along different measurement directions $d_n$ is somewhat analogous to adding extra simultaneous equations to said Analysis problem, in that each further addition to the available data set essentially serves to decrease the degeneracy of the underlying problem.

Spectral model $O_n'$ generically treats B and $L_p$ as different functions of $d_n$. In a particular embodiment of the invention, explicit allowance is made for absorption effects in the specimen, which are also dependent on emission direction (and, correspondingly, on $d_n$). In an example of such an embodiment, spectral model $O_n'$ is expressed in the form:

$$O_n'=A(d_n)*R(d_n)$$

$$R(d_n)=[L_p+B(d_n)]$$

in which $A(d_n)$ is an absorption function, $R(d_n)$ is a radiation function, and the "*" symbol indicates a mathematical convolution. Such a model expresses the following aspects:

Absorption A has a blanketing effect on both $L_p$ and B: regardless of the physical source of an X-ray photon within a specimen, it will be subject to absorption effects therein.

Absorption A has a dependency on $d_n$ (angular dependency): this is because emission direction determines the length of the path followed by an emitting X-ray photon within the specimen, which in turn affects the chance of absorption (attenuation) of that photon.

$L_p$ is essentially intrinsically isotropic/angularly independent (before considering absorption effects). On the other hand, B tends to have an intrinsic angular dependency.

In a specific embodiment of the inventive technique, the employed deconvolution method comprises, for each value of n, computationally determining a minimum divergence:

$$\min \text{div}(O_n\|O_n')=\min \text{div}(O_n\|A(d_n)*[L_p+B(d_n)])$$

between $O_n$ and $O_n'$, wherein one solves for $L_p$ while applying constraints on $A(d_n)$. Certain aspects of this embodiment will now be considered in more detail:

(i) If one assumes no knowledge about A or R, then one obtains a blind deconvolution task. On the other hand, if one can apply some constraints on the absorption function A (see item (ii) below), then one need only optimize for the radiation function R, resulting in the following simultaneous optimization tasks (for a measurement series n=[1, . . . , N], acquired along different measurement directions $d_n$ [and, thus, corresponding to different emission directions]):

$$\min \text{div}(O_1\|A(d_1)*R(d_1)),$$

. . . .

$$\min \text{div}(O_N\|A(d_N)*R(d_N)).$$

Deconvolution results in extraction of the series [R($d_1$), . . . , R($d_N$)]. Since each member of this series is an equation $R(d_n)=[L_p+B(d_n)]$, one obtains a solvable set of simultaneous equations in $L_p$.

(ii) Possible constraints that can be applied to the values $A(d_n)$ to allow the simplification alluded to in item (i) might, for example, include one or more of the following:

(a) Modeling of the absorption function as a parameterized function with a limited number of model parameters, on the basis of which at least a set of values $A(d_n)$ can be estimated. Here, one attempts to intuitively estimate what mathematical form function A might have, and then construct a parameterized model on this basis. A similar approach is used to construct, for example, climate change models, or behavioral models of crowds. By definition, the outcome of such a model will be a simplification, but it will allow a good general grasp of the basic conduct of the system being investigated.

(b) Computational simulation of at least a set of values $A(d_n)$. Here, mathematical techniques are used to emulate the absorptive interaction of X-ray photons and specimen materials, allowing the form of function A to be calculated and representative values $A(d_n)$ to be predicted. The accuracy and extent of the simulation outcome will depend inter alia on the computational/computer resources dedicated to the task in question. Examples of mathematical simulation techniques suitable for this purpose are Monte Carlo methods, Finite Element Analysis, etc.

(c) Empirical determination of at least a set of values $A(d_n)$. Here, use is made of observations of the actual behavior of X-ray photons in given materials. Such observations may, for example, be the outcome of actual measurement sessions performed on other specimens, or of specific experiments performed on homogeneous material specimens, etc. For example, when employing the current invention on a semiconductor specimen comprising a portion of a silicon wafer on which various patterned metallic and dielectric layers have been deposited, one might derive a collection of A-values from one or more of the following:

Other measurement sessions performed on similar semiconductor specimens;

Specific "calibration tests" performed on blank silicon wafers;

Investigative experiments performed using various test coatings on silicon wafers, etc.

(d) Logical solution space limitation, whereby theoretically possible values $A(d_n)$. that are judged to be physically meaningless (e.g. negative values) are discarded. Here, one seeks to intuitively limit the size of a possible solution space by "weeding out" results that are theoretically possible but that are adjudged to be devoid of physical reality. For example, one might constrain the function A to yield only positive values, or restrict it to a differential (i.e. smoothly varying) functional form, or place limits on its statistical dependence, etc.

(e) Inference of a second set of values $A(d_n)$ by applying extrapolation and/or interpolation to a first set of values $A(d_n)$. Here, having obtained a first set of A-values $\{A(d_n)\}_1$, a second set of A-values $\{A(d_n)\}_2$ is derived therefrom on the basis of extrapolation and/or interpolation. For example, if the elements of $\{A(d_n)\}_1$ are observed to lie on a smooth, monotonic curve, one can use interpolation to infer the positions of intermediate elements and/or extrapolation to infer the positions of boundary elements of the set.

It is noted that points (a)-(e) would similarly apply to a situation in which constraints were to be placed on $R(d_n)$ instead of $A(d_n)$.

(iii) The minimum divergence referred to in point (i) could, for example, be selected from techniques such as the Least Squares Distance, Csiszar-Morimoto F-divergences, Bregman Divergences, Alpha-Beta-Divergences, the Bhattacharyya Distance, the Cramér-Rao Bound, and various derivatives, hybrids and combinations of these. The particular choice of the type of divergence can depend inter alia on the statistical nature of the assumed noise in the computation in question; for example:

In the particular case of Gaussian noise, one could elect to minimize the Least Squares distance (also called the Mean Squares distance):

$\min\|O_n - O_n'\|^2$.

In the case of Poisson noise, the Kullback-Leibler divergence (see below) may be a more appropriate choice.

For other noise models, one could use one of the other divergence measures referred to above.

With regard to these broad divergence classes, the following can be noted:

Csiszar-Morimoto F-divergences (and derived measures) include the I and J Kullback-Leibler divergences, the Total Variation, Harmonic Mean, and Chi-Square measures, as well as several other entropy-based measures.

Bregman Divergences (and derived measures) include inter alia the Mahalonobis distance.

Alpha-Beta-Divergences (and derived measures) include measures such as the generalized Kullback-Leibler, Triangular Discrimination, and Arithmetic Geometric measures.

The Bhattacharyya Distance measures the similarity of two discrete or continuous probability distributions.

(iv) The actual minimization (i.e. optimization) of the chosen divergence can be performed using a variety of techniques, such as Matrix Factorization, (non-linear) Independent Component Analysis (ICA), Gradient-Descent methods, Stochastic methods, and Expectation-Maximization Maximum Likelihood (EMML) and Maximum A Priori (MAP) methods, for example. Iterative techniques which use derivatives, among which the Gradient Descent method, Conjugate Gradient method, Newton's method, the Quasi-Newton method, the Levenberg-Marquardt method, and Interior Point methods are some of the most commonly used; the convergence of such methods can be ensured by employing Line-Searches and Trust-Region methods, for example. As an alternative to gradient-based iterative techniques, one can employ optimization heuristics that impose fewer or no constraints on the functions to be optimized. Such heuristic methods search for solutions by relying mostly on stochastic strategies. Examples include Simulated Annealing, Evolutionary Algorithms, the Tabu Search, and Particle Swarm Optimization. Other popular heuristics include the Nelder-Mead Simplex and Hill Climbing algorithms, for example.

It should be noted that, if the input beam impinges perpendicularly on a surface S' of the specimen, then, in many cases (e.g. in which possible complications due to crystalline orientation can be ignored), it will suffice to define a given measurement direction $d_n$ in terms of an associated elevation angle (altitude angle) $\alpha_n$ that it subtends with the surface S'; in other words, in such cases, one can assume rotational symmetry about the propagation axis C' of the input beam, and therefore discount the effect of different azimuthal angles (orbital angles) about location P. However, one can also conceive situations in which said rotational symmetry is broken (e.g. in certain cases with an obliquely incident input beam, and/or complications associated with crystalline orientation), in which case measurement directions $d_n$ at different azimuthal angles might be useful. The skilled artisan will understand this point, and will be able to choose a set d of mutually different (disparate/heterogeneous) measurement directions $d_n$ that is matched to the particulars/needs of a given spectral investigation.

With reference to item (ii)(a) above, the aforementioned absorption function $A(d_n)$ can, for example, be modelled according to:

$$A(d_n) \sim \frac{A_M(E)}{1 - \exp(-A_M(E)K \operatorname{cosec}\alpha_n)}$$

where:

$A_M(E)$ is a mass absorption coefficient for photon energy E: see, for example:
en.wikipedia.org/wiki/Mass_attenuation_coefficient $\alpha_n$ is an elevation angle between direction $d_n$ and a surface (S') of the specimen onto which said input beam is directed;

K is a proportionality constant.

As regards the actual accrual/acquisition of the measurement set $M=\{(O_n, d_n)\}$ for the various values of $d_n$ in the set d, there are several possible approaches. In one possible approach:

Said detector arrangement comprises a plurality of sub-detectors $\{S_n\}$ that are angularly distributed about said specimen holder, whereby each sub-detector $S_n$ registers X-rays emanating along associated direction $d_n$ to yield associated output value $O_n$;

The measurement set M is compiled by simultaneously acquiring its component data pairs $(O_n, d_n)$.

Figure 2:
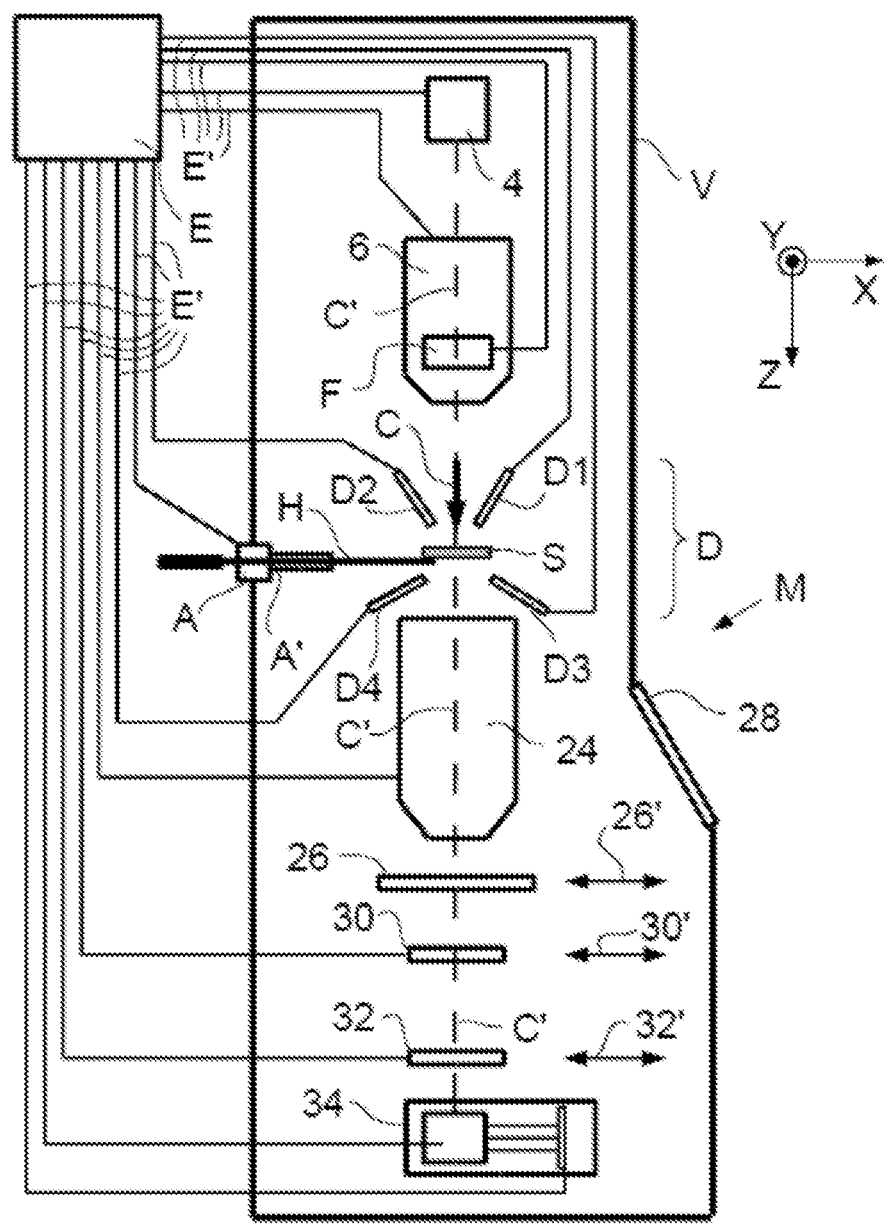
Figure 3:
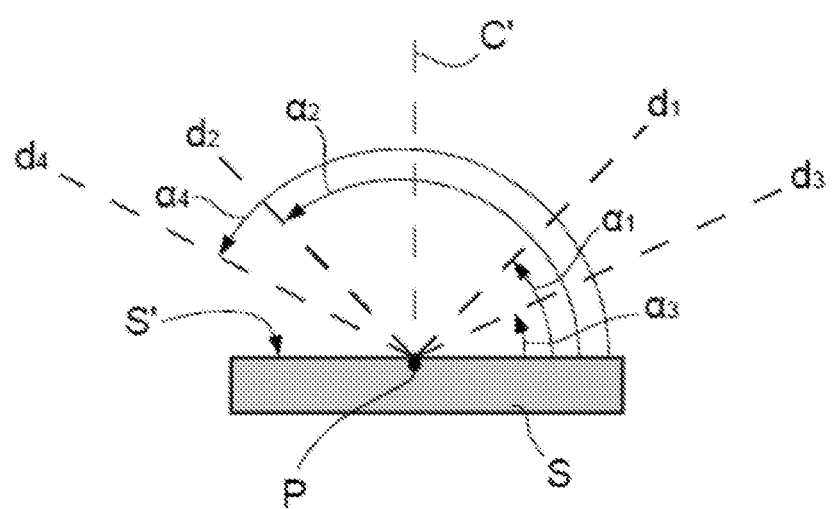

Such a set-up uses a cluster of sub-detectors to capture the various values $O_n$ at (substantially) the same time. These sub-detectors $\{S_n\}$ may be individual/discrete devices, or they may be different zones of a single device that has position-dependent detection functionality. For example:

One could employ a cluster (group, collection) of individual SDD detectors, arranged along different angular directions relative to the specimen. Such a scenario is illustrated in FIGS. 1-3, for example.

Alternatively/supplementally, one could place a single detector—with a relatively large detection surface—near the specimen, in such a manner that different designated zones of the device are located along different angular directions from the specimen.

Since measurement set M is accrued via simultaneous data collection along the various measurement directions $d=\{d_n\}$, this embodiment has the advantage of being intrinsically fast in nature.

As an alternative embodiment to that that in the previous paragraph, one can also conceive a set-up in which:

Said detector arrangement comprises a unitary detector and an associated adjustment mechanism that allows said detector to be selectively aligned along different directions $d_n$ in the set d;

The measurement set M is compiled by sequentially acquiring its component data pairs ($O_n$, $d_n$).

The adjustment mechanism referred to here could, for example, comprise:

(A) Means for angularly moving the unitary detector relative to the specimen; or (B) Means for adjusting an angular orientation of the specimen relative to the unitary detector, or combinations hereof. In these examples, it is noted that:

As regards (A): One way of achieving such adjustability might, for example, be to fix the unitary detector to a slider that can be moved (e.g. by an actuator) along a (semi-) circular rail that is (approximately) centered on the specimen; in such a manner, one could, for example, adjust the elevation angle α. If such a rail could additionally be rotated about one of its diameters, for example, then this could additionally allow adjustment of azimuthal angle ϕ.

As regards (B): Specimen holders for use in electron microscopes (for example) conventionally allow (some degree of) specimen tilt. Tilting a specimen in this manner adjusts the stance of its irradiated surface S' relative to a given (fixed) detector, thus changing the orientation of the detector as perceived from irradiated location P, and thereby changing $d_n$.

It should be noted that use of the term "unitary detector" in this context does not preclude a plurality of detectors from being used, if so desired; instead, such use is intended to indicate that a single detector can successfully be used for the purposes of the present invention.

There are circumstances in which one could suffice with a spectroscopic measurement at just one location P on a specimen, e.g. in the case of (a portion of) a specimen that was known to be substantially homogeneous. However, in general, one will want to obtain a spectrum from a series of different locations on the specimen, particularly for specimens that are (known/suspected to be) non-homogeneous. Such a measurement series can be conducted manually, but, in general, is more conveniently conducted in an automatic/autonomous manner, e.g. whereby a pre-programmed (or random) sequence of specimen locations is automatically visited and irradiated, with automatic acquisition and deconvolution of an X-ray spectrum at each location. Such an approach is particularly (though not exclusively) useful in mineralogical studies, for example.

The invention will now be elucidated in more detail on the basis of exemplary embodiments and the accompanying schematic drawings, in which:

FIG. 1 renders a cross-sectional view of an embodiment of a scanning-type charged particle microscope in which the present invention can be enacted.

FIG. 2 renders a cross-sectional view of an embodiment of a transmission-type charged particle microscope in which the present invention can be enacted.

FIG. 3 renders a magnified view of a portion of the subject of FIG. 1.

In the Figures, where pertinent, corresponding parts may be indicated using corresponding reference symbols.

EMBODIMENT 1

One intuitive way to consider the non-linear deconvolution task at hand is to formulate it using so-called Bayesian statistics.

One first defines a number of probabilities that will be used throughout the elucidation below, whereby the following shorthand notation is introduced:

$A(d_n)$ may be written as $A_n$;
$R(d_n)$ may be written as $R_n$;
$B(d_n)$ may be written as $B_n$.

One can then set forth the following:

$Pr(R_n|O_n)$ is the probability of distilling the spectral components $R_n$ given the recorded output values $O_n$. The spectral components $R_n$ comprise Bremsstrahlung components $B_n$ and discrete (characteristic line) spectral component $L_p$.

$Pr(R_n)$ is the prior probability associated with the spectral components $R_n$, representing available knowledge about the structure to be reconstructed.

$Pr(O_n)$ is the probability associated with the acquired spectra; however, this is essentially a constant, given that the spectra $O_n$ are actually observed/measured values.

Using Bayes' rule one now obtains:

$$Pr(R_n \mid O_n) = \frac{Pr(O_n \mid R_n) Pr(R_n)}{Pr(O_n)} \qquad (1)$$

In the Bayesian framework, the current problem can be expressed as the following maximization task:

$$\widehat{R_n} = \mathrm{argmax}_{R_n \geq 0} \{Pr(R_n|O_n)\}, \qquad (2)$$

in which one needs to enforce the positivity of the reconstructed variable $R_n$. This is necessary in order to obtain a physically meaningful solution. More commonly, one will use the so called log-likelihood function to simplify the calculations:

$$\widehat{R_n} = \mathrm{argmin}_{R_n \geq 0} \{-\log(Pr(R_n|O_n))\} \qquad (3)$$

As regards its statistical nature, the data recording (detection) process in the current invention is well represented by a Poisson process; given the nature of charged-particle and X-ray detectors, one can assume that each element of the recorded spectra $O_n$ is formed by the realization of independent Poisson processes. This leads to:

$$Pr(R_n \mid O_n) = \prod_{x \in \Omega} \frac{((A_n * R_n)(x))^{O_n(x)} \exp(-(A_n * R_n)(x))}{O_n(x)!}, \qquad (4)$$

wherein it should be noted that "x" is not the linear Cartesian coordinate X, but is instead an algebraic denotation of (three-dimensional) position.

To recover the spectral components $R_n$, one needs to minimize the criterion:

$$J((R_n \mid O_n)) = -\log(Pr(R_n \mid O_n)) \qquad (5)$$

$$= \sum_{x \in \Omega} ((A_n * R_n)(x)) - O_n(x) \cdot \log((A_n * R_n)(x)) + \log(O_n(x)!)$$

Given that the $\Sigma_{x \Delta \Omega} \log(O_n(x)!)$ term does not contain any variables, the criterion can be redefined as:

$$J((R_n|O_n)) = \Sigma_{x \Delta \Omega}((A_n * R_n)(x)) - O_n(x) \cdot \log((A_n * R_n)(x)) \qquad (6)$$

It is important to note that this criterion is related to Kullback-Leibler generalized I-divergence $IDIV(O_n\|R_n)$. This can be seen from the definition of I-divergence:

$$IDIV(O_n\|R_n) \stackrel{def}{=} \sum_{x \in \Omega} O_n(x) \log\left(\frac{O_n(x)}{(A_n * R_n)(x)}\right) - \sum_{x \in \Omega} (O_n(x) - (A_n * R_n)(x)) \quad (7)$$

from which one can obtain:

$$IDIV(O_n\|R_n) = J((R_n|O_n)) - \Sigma_{x \Delta \Omega} O_n(x) \cdot \log(O_n(x)) \quad (8)$$

The second term in (8) is a constant with regard to minimization and, hence, minimizing $J((R_n|O_n))$ is equivalent to minimizing $IDIV(O_n\|R_n)$.

Reference is now made to the following journal article:
[1] H. Lantéri, M. Roche, C. Aime, *"Penalized maximum likelihood image restoration with positivity constraints: multiplicative algorithms, Inverse Problems,"* vol. 18, pp. 1397-1419, 2002, in which it was shown that a positivity-constrained minimization problem of the type (2) above can be solved using the following iterative scheme:

$$R^{l+1}(x) = R^l(x) \cdot \left(\frac{O_n(x)}{(A_n * R^l)(x)} * A_n(-x)\right) \quad (9)$$

This algorithm is also known as the Maximum-Likelihood Expectation Maximization algorithm, which is further described, for example, in the following references:
[2] L. Shepp, Y. Vardi, *"Maximum-Likelihood reconstruction for emission tomography,"* IEEE Transactions on Medical Imaging, MI-5, pp. 16-22, 1982.
[3] Richardson, William Hadley. *"Bayesian-Based Iterative Method of Image Restoration"*, JOSA 62 (1), pp 55-59, 1972.

Convergence in expression (9) can be accelerated by using the exponent q as follows:

$$R^{l+1}(x) = R^l(x) \cdot \left(\frac{O_n(x)}{(A_n * R^l)(x)} * A_n(-x)\right)^q \quad (10)$$

Typically, $q \in [1, 1.5]$ and, in addition to acceleration, it can act as a regularizing factor. In the current case, the iterative algorithm needs to be sequentially used for all values $A_n$ associated with the different measurements. Convergence can be assessed empirically or based on other criteria, such as the relative change in the variables.

If one needs to recover or adjust the values of $A_n$, one can use alternate minimization of $R_n$ and $A_n$. One then obtains the following algorithm:

$$R^{l+1}(x) = R^l(x) \cdot \left(\frac{O_n(x)}{(A_n^l * R^l)(x)} * A_n^l(-x)\right)^q \quad (11)$$

$$A_n^{l+1}(x) = A_n^l(x) \cdot \left(\frac{O_n(x)}{(A_n^l * R^{l+1})(x)} * R^{l+1}(-x)\right)^q$$

One can choose to have more iterations for the variables $A_n$ or $R_n$ at each cycle; such a choice can be determined based on experience/experimentation. For example, if it is generally noticed that $R_n$ tends to converge faster, then more iterations can be spent searching for the different values $A_n$.

If prior knowledge about the variables $A_n$ or $R_n$ is available, it can be incorporated into the Bayesian formulation using a combination of conditional $Pr(.|.)$ and joint probabilities $Pr(.,.)$ as follows:

$$Pr(R_n, A_n | O_n) = \frac{Pr(O_n | R_n, A_n) Pr(R_n) Pr(A_n)}{Pr(O_n)} \quad (12)$$

It follows that the minimization problem (2) is then modified as follows:

$$\hat{V} = \text{argmax}_{V \geq 0}\{Pr(V, K_n | O_n)\} \quad (13)$$

and the log-likelihood criterion to be minimized then becomes $$J(R_n, A_n | O_n) = -\log(Pr(O_n | R_n, A_n)) - \log(Pr(R_n)) - \log(Pr(A_n)) \quad (14)$$
$$= J(O_n | R_n, A_n) + J(R_n) + J(A_n)$$

While the first term is the data term that ensures that one fits the observations, the second and third terms are known as regularization terms that use knowledge and assumptions about the variables to limit the space of solutions and reduce the effects of noise. The criterion $J(R_n, A_n | O_n)$ can be minimized using the Maximum Likelihood Expectation Maximization approach. Optimization can be also carried using a variety of other convex and non-convex methods, as set forth, for example, in the following reference:
[4] William H. Press, Saul A. Teukolsky, William T. Vetterling, Brian P. Flannery, *Numerical Recipes in C: The Art of Scientific Computing*, Second Edition (1992).

For completeness, it is noted that the approach set out in the current Embodiment can be regarded as a hybrid/variant of the so-called Richardson-Lucey Algorithm (RLA). The RLA is a known mathematical technique that can be applied to solve a variety of problems. For example, it was used by NASA scientists in an attempt to computationally improve blurred imagery from the original (i.e. uncorrected) Hubble Space Telescope.

EMBODIMENT 2

FIG. 2 is a highly schematic depiction of an embodiment of a CPM according to the present invention; more specifically, it shows an embodiment of a scanning-type microscope M, which, in this case, is a SEM (though, in the context of the current invention, it could just as validly be an ion-based microscope, for example). The microscope M comprises a particle-optical column/illuminator 1, which produces a beam C of input charged particles (in this case, an electron beam) that propagates along a particle-optical axis C'. The particle-optical column 1 is mounted on a vacuum chamber V, which comprises a specimen holder H and associated stage/actuator A for holding/positioning a specimen S. The vacuum chamber V is evacuated using vacuum pumps (not depicted). With the aid of voltage source 17, the specimen holder H, or at least the specimen S, may, if desired, be biased (floated) to an electrical potential with respect to ground.

The particle-optical column 1 comprises an electron source 9 (such as a Schottky emitter), lenses 11, 13 to focus the electron beam C onto the specimen S, and a deflection unit F (to perform beam deflection/scanning of the beam C). The apparatus M further comprises a controller/computer processing apparatus E for controlling inter alia the deflection unit F, lenses 11 and 13, X-ray detector arrangement D (=individual detectors D1+D2+D3+D4), and electron detector D', and displaying information gathered from the X-ray detector arrangement D/electron detector D' on a display unit 27.

The items D, D' are chosen from a variety of possible detector types that can be used to examine different types of "stimulated" output radiation flux emanating from the specimen S in response to irradiation by the input beam C. In the apparatus depicted here, the following detector choices have been made:

- In detector arrangement D, each of the individual sub-detectors D1, D2, D3, D4 is a silicon drift detector (SDD) that is used to detect a flux of X-rays emanating from the specimen S; alternatively, a Silicon Lithium (Si(Li)) detector, for example, could be used for this purpose. As here depicted, there are four sub-detectors D1-D4, though one could just as easily choose a different number of sub-detectors.
- Alternatively/supplementally, one could elect to detect X-rays using a movable unitary detector, and/or a stationary unitary detector in combination with a variety of different tilts of the specimen holder H.
- Detector D' is a segmented electron detector, comprising a plurality of independent detection segments (e.g. quadrants) disposed about a central aperture 23 (allowing passage of the beam C). Such a detector can, for example, be used to investigate (the angular dependence of) a flux of output (secondary or backscattered) electrons emerging from the specimen S.

As a supplement to the depicted X-ray detector arrangement D and electron detector D', one could, if desired, also elect to detect other types of output radiation emanating from the specimen S, such as cathodoluminescence, for instance. One could also elect to use a different type of electron detector D', such as a boron-doped solid state detector, for instance.

By scanning the input beam C over the specimen S, output radiation—generally comprising, a flux of X-rays, infrared/visible/ultraviolet light, secondary electrons and backscattered (BS) electrons—emanates from the specimen S. Since such output radiation is position-sensitive (due to said scanning motion), the information obtained from the X-ray detector arrangement D/electron detector D' will also be position-dependent. This fact allows the output of:

- Electron detector D' to be used to produce an electron image of (part of) the specimen S, which image is basically a map of an output of detector D' as a function of scan-path position on the specimen S.
- One or more of sub-detectors D1, D2, D3, D4 to be used to yield a position-dependent EDX spectrum of (part of) the specimen S.

The signals from items D, D' pass along control lines (buses) E', are processed by the controller E, and displayed on display unit 27. Such processing may include operations such as combining, integrating, subtracting, false colouring, edge enhancing, and other processing known to the skilled artisan. In addition, automated recognition processes (e.g. as used for particle analysis) may be included in such processing.

It should be noted that many refinements and alternatives of such a set-up will be known to the skilled artisan, including, but not limited to:

- The use of dual beams—for example an electron beam C for imaging and an ion beam for machining (or, in some cases, imaging) the specimen S;
- The use of a controlled environment at the specimen S—for example, maintaining a pressure of several mbar (as used in a so-called Environmental SEM) or by admitting gases, such as etching or precursor gases, etc.

Turning now to FIG. 3, this more clearly depicts the different measurement directions $d_1$, $d_2$, $d_3$, $d_4$ that are respectively associated with sub-detectors D1, D2, D3, D4. For a given stance/orientation of the irradiated surface S' of the specimen S (which is horizontal in FIG. 3, but could possibly be adjusted by appropriately tilting the holder H of FIG. 1), these measurement directions have associated elevation angles $\alpha_1$, $\alpha_2$, $\alpha_3$, $\alpha_4$, respectively (which are measured in the XZ plane of FIG. 1).

EMBODIMENT 3

FIG. 3 is a highly schematic depiction of an embodiment of another CPM according to the current invention; more specifically, it shows an embodiment of a transmission-type microscope M, which, in this case, is a TEM/STEM (though, in the context of the current invention, it could just as validly be an ion-based microscope, for example). In the Figure, within a vacuum enclosure V, an electron source 4 (such as a Schottky emitter, for example) produces a beam (C) of electrons that traverse an electron-optical illuminator 6, serving to direct/focus them onto a chosen part of a specimen S (which may, for example, be (locally) thinned/planarized). This illuminator 6 has an electron-optical axis C', and will generally comprise a variety of electrostatic/magnetic lenses, (scan) deflector(s) F, correctors (such as stigmators), etc.; typically, it can also comprise a condenser system (in fact, the whole of item 6 is sometimes referred to as "a condenser system").

The specimen S is held on a (rod-like) specimen holder H that seats into a cradle A' (such as the FEI CompuStage) connected to a positioning device (stage, actuator) A; this cradle A' can typically be moved/positioned in X, Y, Z, and can also often be rotated about X and/or Y (see the depicted Cartesian coordinate system). Such positioning allows different parts of the specimen S to be irradiated/imaged/inspected by the electron beam traveling along axis C', and also allows the specimen S to be tilted as part of a tomographic measurement series (sinogram acquisition), for example; in principle, it also allows scanning motion to be performed, as an alternative to beam scanning.

The (focused) electron beam C traveling along axis C' will interact with the specimen S in such a manner as to cause various types of "stimulated" radiation flux to emanate from the specimen S, including (for example) secondary electrons, backscattered electrons, X-rays and optical radiation (cathodoluminescence). If desired (as is the case in the current invention), one or more of these radiation types can be detected; in the current case, each of the sub-detectors D1, D2, D3, D4 is an EDX detector—such as an SDD or Si(Li) detector, for example—which together comprise a detector arrangement D, and which (individually or in groups) allow an EDX spectrum to be acquired, in much the same way as in Embodiment 2 above (SEM). However, in addition, one can study electrons that traverse (pass through) the specimen S, emerge (emanate) from it and continue to propagate (substantially, though generally with some deflection/scattering) along axis C'. Such a transmitted electron flux enters an imaging system (combined objective/projection lens) 24, which will generally comprise a variety of electrostatic/magnetic lenses, deflectors, correctors (such as stigmators), etc. In normal (non-scanning) TEM mode, this imaging system 24 can focus the transmitted electron flux onto a fluorescent screen 26, which, if desired, can be retracted/withdrawn (as schematically indicated by arrows 26') so as to get it out of the way of axis C'. An image (or diffractogram) of (part of) the specimen S will be formed by imaging system 24 on screen 26, and this may be viewed through viewing port 28 located in a suitable part of a wall of enclosure V. The retraction mechanism for screen 26 may, for example, be mechanical and/or electrical in nature, and is not depicted here.

As an alternative to viewing an image on screen 26, one can instead make use of the fact that the depth of focus of the electron flux emerging from imaging system 24 is generally quite large (e.g. of the order of 1 meter). Consequently, various other types of analysis apparatus can be used downstream of screen 26, such as:

- TEM camera 30. At camera 30, the electron flux can form a static image (or diffractogram) that can be processed by controller E and displayed on a display device (not depicted), such as a flat panel display, for example. When not required, camera 30 can be retracted/withdrawn (as schematically indicated by arrows 30') so as to get it out of the way of axis C'.
- STEM recorder 32. An output from recorder 32 can be recorded as a function of (X,Y) scanning position of the beam C on the specimen S, and an image can be constructed that is a "map" of output from recorder 32 as a function of X,Y. Recorder 32 can comprise a single pixel with a diameter of e.g. 20 mm, as opposed to the matrix of pixels characteristically present in camera 30. Moreover, recorder 32 will generally have a much higher acquisition rate (e.g. $10^6$ points per second) than camera 30 (e.g. $10^2$ images per second). Once again, when not required, recorder 32 can be retracted/withdrawn (as schematically indicated by arrows 32') so as to get it out of the way of axis C' (although such retraction would not be a necessity in the case of a donut-shaped annular dark field recorder 32, for example; in such a recorder, a central hole would allow beam passage when the recorder was not in use).
- As an alternative to imaging using camera 30 or recorder 32, one can also invoke spectroscopic apparatus 34, which could be an EELS module, for example (EELS=Electron Energy-Loss Spectroscopy).

It should be noted that the order/position of items 30, 32 and 34 is not strict, and many possible variations are conceivable. For example, spectroscopic apparatus 34 can also be integrated into the imaging system 24.

Note that the controller (computer processor) E (which may have a unitary or composite structure, as desired) is connected to various illustrated components via control lines (buses) E'. This controller E can provide a variety of functions, such as synchronizing actions, providing setpoints, processing signals, performing calculations, and displaying messages/information on a display device (not depicted). The skilled artisan will understand that the interior of the enclosure V does not have to be kept at a strict vacuum; for example, in a so-called "Environmental TEM/STEM", a background atmosphere of a given gas is deliberately introduced/maintained within the enclosure V. The skilled artisan will also understand that, in practice, it may be advantageous to confine the volume of enclosure V so that, where possible, it essentially hugs the axis C', taking the form of a small tube (e.g. of the order of 1 cm in diameter) through which the employed electron beam passes, but widening out to accommodate structures such as the source 4, specimen holder H, screen 26, camera 30, recorder 32, spectroscopic apparatus 34, etc.

As depicted in FIG. 2, there are four sub-detectors D1-D4, though one could just as easily choose a different number of sub-detectors. Moreover, one could choose to locate different numbers (than those depicted) of these sub-detectors D1-D4 above/below the specimen S. Alternatively/supplemental, one could elect to detect X-rays using a movable unitary detector, and/or a stationary unitary detector in combination with a variety of different tilts of the specimen holder H.

The invention claimed is:

1. A method of examining a specimen using a spectroscopic apparatus, comprising the following steps:
providing the specimen on a specimen holder;
directing a focused input beam of radiation onto a location P on the specimen, thereby producing an interaction that causes a flux of X-rays to emanate from said location;
examining said flux using a detector arrangement, thus accruing a measured spectrum for said location;
choosing a set of different measurement directions $d=\{d_n\}$ that originate from P, where n is a member of an integer sequence;
recording an output $O_n$ of said detector arrangement for different values of dn, thus compiling a measurement set $M=\{(O_n, d_n)\}$;
adopting a spectral model $O_n'$ for $O_n$ that is a convoluted mix of terms $B(d_n)$ and $L_p$, where:
$B(d_n)$ is a substantially continuous spectral component associated with Bremsstrahlung;
$L_P$ is a substantially discrete spectral component associated with the composition of the specimen at location P;
automatically deconvolving the measurement set M on the basis of said spectral model $O_n'$ and distill Lp therefrom, wherein spectral model $O_n'$ is expressed in the form:

$$O_n'=A(dn)*R(dn)$$

$$R(dn)=[Lp+B(dn)]$$

in which A(dn) is an absorption function, accounting for the dependence of x-ray absorption as a function of the path length within the specimen, * is a mathematical convolution and R(dn) is a radiation function comprising the types of x-ray emitted from the specimen.

2. The method according to claim 1, wherein said deconvolution comprises, for each value of n, computationally determining a minimum divergence:

$$\min \operatorname{div}(O_n \| O_n') = \min \operatorname{div}(O_n \| A(d_n)*[L_P+B(d_n)])$$

between $O_n$ and $O_n'$, wherein one solves for $L_p$ while applying constraints on $A(d_n)$.

3. The method according to claim 1, wherein $A(d_n)$ is modelled according to:

$$A(d_n) \sim \frac{A_M(E)}{1-\exp(-A_M(E)K\cosec\alpha_n)}$$

where:
$A_M(E)$ is a mass absorption coefficient for photon energy E;
$\alpha_n$ is an elevation angle between direction $d_n$ and a surface of the specimen onto which said input beam is directed;
K is a proportionality constant.

4. The method according to claim 1, wherein:
said detector arrangement comprises a plurality of sub-detectors $\{S_n\}$ that are angularly distributed about said specimen holder, whereby each sub-detector $S_n$ registers X-rays emanating along associated direction $d_n$ to yield associated output value $O_n$; and
the measurement set M is compiled by simultaneously acquiring its component data pairs $(O_n, d_n)$.

5. The method according to claim 1, wherein:
said detector arrangement comprises a unitary detector and an associated adjustment mechanism that allows said detector to be selectively aligned along different directions $d_n$ in the set d; and
the measurement set M is compiled by sequentially acquiring its component data pairs $(O_n, d_n)$.

6. The method according to claim 5, wherein said adjustment mechanism is selected from the group comprising:
means for angularly moving the unitary detector relative to the specimen; and
a tiltable specimen holder for adjusting an angular orientation of the specimen relative to the unitary detector, and combinations hereof.

7. The method according to claim 1, wherein said directing, examining and deconvolving steps are automatically repeated for a series of successive locations on the specimen.

8. The method according to claim 1, wherein said spectrum is selected from the group comprising an EDX spectrum, a PIXE spectrum and an XRF spectrum.

9. A spectroscopic apparatus, comprising:
a specimen holder, for holding a specimen;
a source, for producing an input beam of radiation;
an illuminator, for directing said beam so as to irradiate the specimen;
a detector arrangement, for detecting a flux of X-rays emanating from the specimen in response to said irradiation;
a computer processor, programmed to perform at least one automated procedure in the apparatus, wherein said computer processor programmed to perform the following steps:
choose a set of different measurement directions $d=\{d_n\}$ that originate from P, where n is a member of an integer sequence;
record an output On of said detector arrangement for different values of $d_n$, thus compiling a measurement set $M=\{(On, d_n)\}$;
adopt a spectral model On' for On that is a convoluted mix of terms B and $L_p$, where:
B is a substantially continuous spectral component associated with Bremsstrahlung;
and
$L_P$ is a substantially discrete spectral component associated with the composition of the specimen at location P; and
deconvolve the measurement set M on the basis of said spectral model On' and distill $L_P$ therefrom, wherein spectral model On' is expressed in the form:

$On'=A(dn)*R(dn)$ $R(dn)=[Lp+B(dn)]$ in which $A(d_n)$ is an absorption function, accounting for the dependence of x-ray absorption as a function of the path length within the specimen, * is a mathematical convolution and R(d) is a radiation function comprising the types of x-ray emitted from the specimen.

10. The spectroscopic apparatus according to claim 9, wherein;
said input beam comprises charged particles; and
said apparatus is a charged-particle microscope.

11. The spectroscopic apparatus according to claim 9, wherein;
said detector arrangement comprises a plurality of sub-detectors $\{S_n\}$ that are angularly distributed about said specimen holder.

12. The spectroscopic apparatus of claim 11, wherein each sub-detector $S_n$ registers X-rays emanating along associated direction $d_n$ to yield associated output value $O_n$; and
the computer processor is programmed to compile the measurement set M by simultaneously acquiring its component data pairs $(O_n, d_n)$.

13. The spectroscopic apparatus of claim 11, wherein the sub-detectors $\{S_n\}$ are segments of a larger unitary detector.

14. The spectroscopic apparatus of claim 11, wherein the sub-detectors $\{S_n\}$ are discrete detectors.

15. The spectroscopic apparatus according to claim 9, wherein;
said detector arrangement comprises a unitary detector and an associated adjustment mechanism that allows said detector to be selectively aligned along different directions $d_n$ in the set d; and
the computer processor is programmed to compile the measurement set M by sequentially acquiring its component data pairs $(O_n, d_n)$.

16. The spectroscopic apparatus according to claim 15, wherein said adjustment mechanism comprises an actuator for angularly moving the unitary detector relative to the specimen.

17. The spectroscopic apparatus according to claim 15, wherein said adjustment mechanism comprises an actuator for adjusting an angular orientation of the specimen relative to a fixed unitary detector.

18. The spectroscopic apparatus according to claim 9, wherein said detector arrangement comprises one or more of:
an EDX detector;
a PIXE detector; and
an XRF detector,
and combinations hereof.

19. The spectroscopic apparatus according to claim 9, wherein the computer processor is further programmed to automatically repeat on a series of locations on the specimen, the steps of:
choose a set of different measurement directions $d=\{d_n\}$ that originate from P, where n is a member of an integer sequence;
record an output $O_n$ of said detector arrangement for different values of $d_n$, thus compiling a measurement set $M=\{(O_n, d_n)\}$;
adopt a spectral model $O_n'$ for $O_n$ that is a convoluted mix of terms B and $L_p$, where:
B is a substantially continuous spectral component associated with Bremsstrahlung;
$L_p$ is a substantially discrete spectral component associated with the composition of the specimen at location P; and
deconvolve the measurement set M on the basis of said spectral model $O_n'$ and distill $L_p$ therefrom, on a series of locations on the specimen.

* * * * *